United States Patent [19]
Russo et al.

[11] Patent Number: 5,441,977
[45] Date of Patent: Aug. 15, 1995

[54] 21-NORRAPAMYCIN

[75] Inventors: Ralph J. Russo, Piscataway, N.J.; Stanley R. Howell, San Diego, Calif.; Surendra N. Sehgal, Princeton, N.J.

[73] Assignee: American Home Products Corporation, Madison, N.J.

[21] Appl. No.: 204,028

[22] Filed: Mar. 1, 1994

Related U.S. Application Data

[63] Continuation-in-part of Ser. No. 949,964, Sep. 24, 1992, abandoned.

[51] Int. Cl.⁶ .................. C07D 498/16; A61K 31/40
[52] U.S. Cl. .................... 514/411; 540/456
[58] Field of Search .................. 540/456; 514/411

[56] References Cited

U.S. PATENT DOCUMENTS

| | | | |
|---|---|---|---|
| 3,929,992 | 12/1975 | Sehgal et al. | 424/122 |
| 3,993,749 | 11/1976 | Sehgal et al. | 424/122 |
| 4,316,885 | 2/1982 | Rakhit | 424/122 |
| 4,375,464 | 3/1983 | Sehgal et al. | 424/122 |
| 4,401,653 | 8/1983 | Eng | 424/114 |
| 4,650,803 | 3/1987 | Stella et al. | 514/291 |
| 4,885,171 | 12/1989 | Surendra et al. | 424/122 |
| 5,078,999 | 1/1992 | Warner et al. | 424/122 |
| 5,080,899 | 1/1992 | Sturm et al. | 424/122 |
| 5,091,389 | 2/1992 | Ondeyka et al. | 514/291 |
| 5,100,883 | 3/1992 | Schiehser | 424/183 |
| 5,100,899 | 3/1992 | Calne | 514/291 |
| 5,102,876 | 4/1992 | Caufield | 514/183 |
| 5,147,877 | 9/1992 | Goulet et al. | 340/456 |

FOREIGN PATENT DOCUMENTS

| | | | |
|---|---|---|---|
| 478235 | 12/1989 | European Pat. Off. | 540/456 |
| 507555A1 | 7/1992 | European Pat. Off. | 540/456 |
| WO895304 | 6/1989 | WIPO | 540/456 |
| WO912736 | 3/1991 | WIPO | 540/456 |

OTHER PUBLICATIONS

Venzina, C., J. Antibiot. 28:721 (1975).
Sehgal, S. N., J. Antibiot. 28:727 (1975).
Baker, H. J., Antibiot. 31:539 (1978).
Martel, R. R., Can. J. Physiol. Pharmacol. 55:48 (1977).
Staruch, M. J., FASEB 3:3411 (1989).
Dumont, F. J., FASEB 3:5256 (1989).
Calne, R. Y., Lancet 1183 (1978).
Morris, R. E., Med. Sci. Res. 17:877 (1989).
Baeder, W. L., Fifth Int. Conf. Inflamm. Res. Assoc. 121 (Abstract) (1990).
Meiser, B. M., J. Heart Lung Transplant. 11 (pt. 2):197 (1992).

*Primary Examiner*—Robert T. Bond
*Attorney, Agent, or Firm*—Arnold S. Milowsky

[57] ABSTRACT

A compound which is 21-norrapamycin or a pharmaceutically acceptable salt thereof, which is useful as an immunosuppressive, anti-inflammatory, antifungal, antitumor, and antiproliferative agent. 21-Norrapamycin has the following structure.

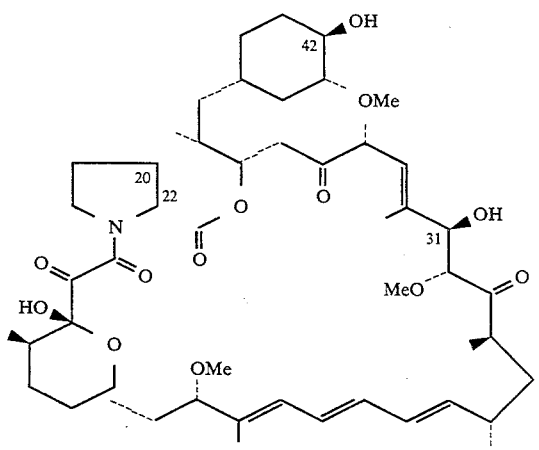

16 Claims, No Drawings

5,441,977

21-NORRAPAMYCIN

CROSS REFERENCE TO RELATED APPLICATIONS

This application is a continuation-in-part of Ser. No. 07/949,964, filed Sep. 24, 1992, now abandoned.

BACKGROUND OF THE INVENTION

This invention relates to an analog of rapamycin, namely 21-norrapamycin, and a method for using 21-norrapamycin to induce immunosuppression and in the treatment or prevention of transplantation rejection, graft vs. host disease, autoimmune diseases, diseases of inflammation, solid tumors, fungal infections, and hyperproliferative vascular disorders.

Rapamycin is a macrocyclic triene antibiotic produced by Streptomyces hygroscopicus, which was found to have antifungal activity, particularly against Candida albicans, both in vitro and in vivo [C. Vezina et al., J. Antibiot. 28, 721 (1975); S. N. Sehgal et al., J. Antibiot. 28, 727 (1975); H. A. Baker et al., J. Antibiot. 31,539 (1978); U.S. Pat. No. 3,929,992; and U.S. Pat. No. 3,993,749].

Rapamycin alone (U.S. Pat. No. 4,885,171) or in combination with picibanil (U.S. Pat. No. 4,401,653) has been shown to have antitumor activity. R. Martel et al. [Can. J. Physiol. Pharmacol. 55, 48 (1977)] disclosed that rapamycin is effective in the experimental allergic encephalomyelitis model, a model for multiple sclerosis; in the adjuvant arthritis model, a model for rheumatoid arthritis; and effectively inhibited the formation of IgE-like antibodies.

The immunosuppressive effects of rapamycin have been disclosed in FASEB 3, 3411 (1989) and its utility in preventing transplantation rejection shown in U.S. Pat. No. 5,100,899. Cyclosporin A and FK-506, other macrocyclic molecules, also have been shown to be effective as immunosuppressive agents, therefore useful in preventing transplant rejection [FASEB 3, 3411 (1989); FASEB 3, 5256 (1989); and R. Y. Calne et al., Lancet 1183 (1978)].

Rapamycin has also been shown to be useful in preventing or treating systemic lupus erythematosus [U.S. Pat. No. 5,078,999], pulmonary inflammation [U.S. Pat. No. 5,080,899], insulin dependent diabetes mellitus [Fifth Int. Conf. Inflamm. Res. Assoc. 121 (Abstract), (1990) and European Patent Application 507,555 A1], and smooth muscle cell proliferation and intimal thickening following vascular injury [Morris, R. J. Heart Lung Transplant 11 (pt. 2): 197 (1992)].

Mono- and diacylated derivatives of rapamycin (esterified at the 28 and 43 positions) have been shown to be useful as antifungal agents (U.S. Pat. No. 4,316,885) and used to make water soluble prodrugs of rapamycin (U.S. Pat. No. 4,650,803). Recently, the numbering convention for rapamycin has been changed; under Chemical Abstracts nomenclature, the above described esters would be at the 31- and 42-positions. 21-Norrapamycin could also be referred to as 19-norrapamycin under the older nomenclature system.

DESCRIPTION OF THE INVENTION

This invention provides a compound which is named 21-norrapamycin or a pharmaceutically acceptable salt thereof, which is useful as an immunosuppressive, anti-inflammatory, antifungal, antitumor, and antiproliferative agent. 21-Norrpamycin has the following chemical structure.

This invention also relates to substantially pure 21-norrapamycin; substantially pure is defined as being in excess of 98% purity and free of rapamycin.

The pharmaceutically acceptable salts are those derived from such inorganic cations such as sodium, potassium, and the like; and organic bases such as: mono-, di-, and trialkyl amines of 1–6 carbon atoms, per alkyl group and mono-, di-, and trihydroxyalkyl amines of 1–6 carbon atoms per alkyl group, and the like.

This invention also provides a pharmaceutical composition for inducing immunosuppression in a mammal in need thereof comprising: a pharmaceutical carrier and a therapeutically effective amount of 21-norrapamycin. This invention further provides a method of inducing immunosuppression in a mammal in need thereof comprising administration to said mammal an immunosuppressive effective amount of 21-norrapamycin.

21-Norrapamycin was prepared by fermentation of a culture of Streptomyces hygroscopicus, NRRL 5491, which can be obtained from the culture collection at the National Center for Agricultural Utilization Research, USDA, ARS, Peoria, Ill. NRRL 5491 can also be obtained from the American Type Culture Collection, Rockville, Md., under ATCC 29253.

21-Norrapamycin can be obtained by aerobic fermentation of NRRL 5491 using standard fermentation, isolation, and purification techniques. Methods for preparing first stage innoculum and fermentation of NRRL 5491 are described in U.S. Pat. No. 3,929,992, which is hereby incorporated by reference. A specific embodiment for the fermentation of NRRL 5491 and isolation and purification of 21-norrapamycin is provided in Example 1. A preferred method for the production of 21-norrapamycin was achieved using precursor enhanced fermentation [Pavia, N. L., J. Nat. Prod. 51: 167 (1991)]. NRRL 5491 was fermented in a defined medium in which the concentration of lysine was limited and the concentration of profine was supplemented, thereby forcing the organism to incorporate profine into the macrofide instead of lysine. Lysine being a precursor of the pipecolic acid moiety that is contained in the rapamycin macrofide. The procedure used for the preparation of 21-norrapamycin using precursor enhanced fermentation is described in Example 2.

Immunosuppressive activity of 21-norrapamycin was established in an in vitro standard pharmacological test procedure which measured the ability of 21-norrapamycin to inhibit lymphocyte proliferation (LAF). Rapamycin was also evaluated for the purpose of comparison. The procedure used and the results obtained are described below.

The comitogen-induced thymocyte proliferation procedure (LAF) was used as an in vitro measure of the immunosuppressive effects of representative compounds. Briefly, cells from the thymus of normal BALB/c mice are cultured for 72 hours with PHA and IL-1 and pulsed with tritiated thymidine during the last six hours. Cells are cultured with and without various concentrations of rapamycin or test compound. Cells are harvested and incorporated radioactivity is determined. Inhibition of lymphoproliferation is assessed as percent change in counts per minute from non-drug treated controls. In two evaluations, $IC_{50}$s of 33.2 and 32.0 nM were obtained for 21-norrapamycin and 7.8 and 7.5 nM for rapamycin. At a doses of 1 $\mu$M and 0.1 $\mu$M, 21-norrapamycin inhibited proliferation by 96% and 90%, respectively. At the same concentrations rapamycin inhibited proliferation by 97% and 96%, respectively.

The results of this standard pharmacological test procedure demonstrates immunosuppressive activity for 21-norrapamycin by virtue of its ability to suppress T-cell proliferation in response to mitogenic stimulation.

Based on its activity profile of 21-norrapamycin is also considered to have antitumor, antifungal, anti-inflammatory, and smooth muscle cell antiproliferative activities.

In particular, 21-norrapamycin is useful in the treatment or inhibition of transplantation rejection such as, kidney, heart, liver, lung, bone marrow, pancreas (islet cells), cornea, small bowel, and skin allografts, and heart valve xenografts; autoimmune diseases such as, lupus, rheumatoid arthritis, diabetes mellitus, myasthenia gravis, and multiple sclerosis; and diseases of inflammation such as, psoriasis, dermatitis, eczema, seborrhea, inflammatory bowel disease, and eye uveitis; solid tumors; fungal infections; pulmonary inflammation, such as asthma, chronic obstructive pulmonary disease, emphysema, acute respiratory distress syndrome, and bronchitis; and disease states involving intimal smooth muscle cell proliferation such as restenosis following biologically or mechanically mediated vascular injury.

Inhibit is used in its dictionary and technical sense as retarding, arresting, or restraining the development or progression of the above disease states.

21-Norrapamycin can also be used in combination with other immunosuppressive agents such as azathioprine, corticosteroids, such as prednisone and methylprednisolone, cyclophosphamide, rapamycin, cyclosporin A, OKT-3, and ATG. By combining 21-norrapamycin with such other drugs or agents for inducing immunosuppression, the toxicity of the latter may be reduced in that lesser amounts of such agents are required to induce immunosuppression. The basis for such combination therapy was established by Stepkowski whose results showed that the use of a combination of rapamycin and cyclosporin A at subtherapeutic doses significantly prolonged heart allograft survival time. [Transplantation Proc. 23:507 (1991)].

21-Norrapamycin can be formulated neat or with a pharmaceutical carrier. The pharmaceutical carrier may be solid or liquid.

A solid carrier can include one or more substances which may also act as flavoring agents, lubricants, solubilizers, suspending agents, fillers, gildants, compression aids, binders or tablet-disintegrating agents; it can also be an encapsulating material. In powders, the carrier is a finely divided solid which is in admixture with the finely divided active ingredient. In tablets, the active ingredient is mixed with a carrier having the necessary compression propennies in suitable proportions and compacted in the shape and size desired. The powders and tablets preferably contain up to 99% of the active ingredient. Suitable solid carriers include, for example, calcium phosphate, magnesium stearate, talc, sugars, lactose, dextrin, starch, gelatin, cellulose, methyl cellulose, sodium carboxymethyl cellulose, polyvinylpyrrolidine, low melting waxes and ion exchange resins.

Liquid carriers are used in preparing solutions, suspensions, emulsions, syrups, elixirs and pressurized compositions. The active ingredient can be dissolved or suspended in a pharmaceutically acceptable liquid carrier such as water, an organic solvent, a mixture of both or pharmaceutically acceptable oils or fats. The liquid carrier can contain other suitable pharmaceutical additives such as solubilizers, emulsifiers, buffers, preservatives, sweeteners, flavoring agents, suspending agents, thickening agents, colors, viscosity regulators, stabilizers or osmo-regulators. Suitable examples of liquid carriers for oral and parenteral administration include water (partially containing additives as above, e.g. cellulose derivatives, preferably sodium carboxymethyl cellulose solution), alcohols (including monohydric alcohols and polyhydric alcohols, e.g. glycols) and their derivatives, and oils (e.g. fractionated coconut oil and arachis oil). For parenteral administration, the carrier can also be an oily ester such as ethyl oleate and isopropyl myristate. Sterile liquid carriers are useful in sterile liquid form compositions for parenteral administration. The liquid carrier for pressurized compositions can be halogenated hydrocarbon or other pharmaceutically acceptable propellant.

Liquid pharmaceutical compositions which are sterile solutions or suspensions can be utilized by, for example, intramuscular, intraperitoneal or subcutaneous injection. Sterile solutions can also be administered intravenously. The compound can also be administered orally either in liquid or solid composition form.

21-Norrapamycin may be administered rectally in the form of a conventional suppository. For administration by intranasal or intrabronchial inhalation or insufflation, 21-norrapamycin may be formulated into an aqueous or partially aqueous solution, which can then be utilized in the form of an aerosol. 21-Norrapamycin may also be administered transdermally through the use of a transdermal patch containing the active compound and a carrier that is inert to the active compound, is non toxic to the skin, and allows delivery of the agent for systemic absorption into the blood stream via the skin. The carrier may take any number of forms such as creams and ointments, pastes, gels, and occlusive devices. The creams and ointments may be viscous liquid or semisolid emulsions of either the oil-in-water or water-in-oil type. Pastes comprised of absorptive powders dispersed in petroleum or hydrophilic petroleum containing the active ingredient may also be suitable. A variety of occlusive devices may be used to release the active ingredient into the blood stream such as a semipermeable membrane covering a reservoir containing the active ingredient with or without a carrier, or a matrix containing the active ingredient. Other occlusive devices are known in the literature.

Preferably, the pharmaceutical composition is in unit dosage form, e.g. as tablets or capsules. In such form, the composition is sub-divided in unit dose containing appropriate quantities of the active ingredient; the unit dosage forms can be packaged compositions, for example, packeted powders, vials, ampoules, prefilled syringes or sachets containing liquids. The unit dosage form can be, for example, a capsule or tablet itself, or it can be the appropriate number of any such compositions in package form. The dosage to be used in the treatment must be subjectively determined by the attending physician.

In addition, 21-norrapamycin may be employed as a solution, cream, or lotion by formulation with pharmaceutically acceptable vehicles containing 0.1-5 percent, preferably 2%, of active compound which may be administered to an affected area.

The dosage requirements vary with the particular compositions employed, the route of administration, the severity of the symptoms presented and the particular subject being treated. Based on the results obtained in the standard pharmacological test procedures, projected daily intravenous dosages of 21-norrapamycin, would be 0.001-100 mg/kg, preferably between 0.005-20 mg/kg, and more preferably between 0.01-2 mg/kg. Projected daily oral dosages of 21-norrapamycin would be 0.005-300 mg/kg, preferably between 0.01-200 mg/kg, and more preferably between 0.05-40 mg/kg.

Treatment will generally be initiated with small dosages less than the optimum dose of the compound. Thereafter the dosage is increased until the optimum effect under the circumstances is reached; precise dosages for oral, parenteral, intranasal, intrabronchial, transdermal, or rectal administration will be determined by the administering physician based on experience with the individual subject treated. In general, 21-norrapamycin is most desirably administered at a concentration that will generally afford effective results without causing any harmful or deleterious side effects.

The following Examples illustrate the preparation of 21-norrapamycin by both conventional means and by precursor enhanced fermentation.

EXAMPLE 1

*Streptomyces hygroscopicus* NRRL 5491 was grown and maintained on oatmeal-tomato paste agar slants (T. G. Pridham, et al., Antibiotic Annual 1956-1957, Medical Encyclopedia Inc., New York, p. 947) and in Roux bottles containing the same medium. Good growth was obtained after 7 days of incubation at 28° C. Spores from one Roux bottle were washed off and suspended into 50 mL of sterile distilled water. This suspension was used to inoculate the first stage innoculum.

First Stage Innoculum. Edenmeyer flasks (500 mL) were filled with 100 mL of the following medium:

| Soybean flour (Archer-Daniels, Midland, Mich. "Special X") | = 4% wt/vol |
|---|---|
| Glucose (Cerelose) | = 2% wt/vol |
| Ammonium sulfate | = 0.3% wt/vol |

-continued

| Calcium carbonate | = 0.15% wt/vol |
|---|---|

The flasks were sterilized at 121° C. for 35 minutes and cooled to 25° C. The flasks were inoculated with 4% (4 mL) of spore suspension described above and incubated on a gyrotary shaker (2 inch stroke) at 240 rpm for 24 hours at 25° C.

Second Stage Innoculum. Twenty-four liter flat bottom flasks containing 3.2 L of the innoculum medium described above at pH 7.1-7.3 were sterilized by autoclaving at 121° C. for 35 minutes, shaken to resuspend the insoluble material and resterilized for another 45 minutes. The flasks were cooled to 25° C. and inoculated with 64 mL of first stage innoculum, placed on a reciprocating shaker (4 inch stroke) set at 65 rpm and incubated for 18 hours at 25° C.

Production Stage. The production stage was run in 250 liter New Brunswick fermenters Model F-250 equipped with automatic antifoam addition system and pH recorder/controller. The fermenters were charged with 160 liters of an aqueous production medium consisting of the following constituents:

| Soybean flour (Archer-Daniels, Midland, Mich. "Special X") | = 3% wt/vol |
|---|---|
| Glucose (Cerelose) | = 2% wt/vol |
| Ammonium sulfate | = 0.1% wt/vol |
| Potassium phosphate (monobasic) | = 0.5% wt/vol |
| Antifoaming Agent ("DF-143-PX" Mazer Chemicals, Inc. Gurnee, Ill.) | = 0.05% wt/vol |

The fermenters were sterilized at 121° C. for 30 minutes, cooled, and the pH was adjusted to 5.8 to 6.2 with ammonium hydroxide. They were then inoculated with one flask (2%) of second stage innoculum and fermentation was allowed to proceed at 25° C., with aeration at 0.25 v/v/min and agitation at 200 rpm.

The pH of the fermentation broth started to drop at 30-35 hours and was controlled at 6.0 until the end of fermentation by the automatic, on demand, addition of ammonium hydroxide. At about 48 hours of propagation, the glucose concentration in the broth dropped to about 0.5%, and continuous addition of 40% glucose solution was started at a rate of 3.75% of fermentation mixture volume per day and continued until the end of fermentation. A titer of about 60 μg/ml, determined by microbiological assay on agar plates seeded with *Candida albicans* was reached in 4 to 5 days. The fermentation was stopped at this point.

Extraction and isolation of the 21-norrapamycin was performed by the following procedure:

The mycelial growth broth was extracted with acetone and evaporated under vacuum until only the aqueous portion remained. The aqueous portion was extracted three times with methylene chloride. The methylene chloride extracts were combined and evaporated under reduced pressure. The residue was dissolved in a small volume of methylene chloride and loaded onto a small plug of silica gel. The silica was flash eluted with a step gradient from 50/50 (v/v) hexane/ethyl acetate through 100% ethyl acetate. A final rinse of the plug was made with acetone. Aliquots of each fraction were evaporated under nitrogen, and redissolved in acetonitrile for analytical HPLC. The samples were loaded onto a Nova Pak C18 15 cm×3.9 mm column (Waters) using dioxane/water (60/40) as the mobile phase with a flow rate of 1.0 mL/min. UV detection at 280 nm was use to measure retention times. 21-Norrapamycin had a retention time of 7.3 min under the above HPLC conditions.

The fractions containing 21-norrapamycin were evaporated and purified by preparative chromatography using a Dynamax 1 inch i.d. C18 column. An isocratic mobile phase of acetonitrile/water (70/30, v/v) was used as the eluant at a flow rate of 15 mL/min. UV detection was at 280 nm. Fractions were checked by analytical HPLC as described above for purity, and the fractions containing 21-norrapamycin were combined, and evaporated to give pure 21-norrapamycin.

Negative ion FAB mass spectrum showed a mixture of m/z=899 and 898 and a fragment ion at m/z=576 (the C-21 to C-1/C-1 to C-29 portion of the macrocycle). A fragment at m/z=590, which arises from the C-32-C-36-C-1-C-23 portion of the molecule was also observed.

$^1$H NMR spectrum (alumina neutralized CDCl$_3$, containing TMS as internal reference, 400 MHz): assigned resonances include methyl resonances at §3.38 ppm (C-41 OCH$_3$), 3.36 ppm (C-32 O-CH$_3$), 3.11 ppm (C-7 OCH$_3$), 1.75 ppm (C-30 vinyl CH$_3$), 1.64 ppm (C-6 vinyl CH$_3$), 1.09 ppm (C-28 secondary CH$_3$), 1.03 ppm (C-36 secondary CH$_3$), 1.01 ppm (C-34 secondary CH$_3$), 0.93 ppm (C-12 secondary CH$_3$), and 0.89 ppm (C-37 secondary CH$_3$). H-22 proton was observed at 5.44 ppm.

EXAMPLE 2

*Streptomyces hygroscopicus* NRRL 5491 was grown and maintained, and the spore suspension prepared as described in Example 1. Seven (7) to 15 days of incubation were sufficient for spore growth and maturation. Spores were then scraped off in the minimum volume of sterile water necessary to obtain a highly viscous innoculum. Approximately 5 mL of this spore suspension was used to inoculate 500 mL of the following medium to which proline and lysine were added to provide enhanced production of 21-norrapamycin.

| | |
|---|---|
| H$_2$O | 1800 mL |
| KH$_2$PO$_4$ | 4 g |
| K$_2$HPO$_4$ | 4 g |
| NaCl | 10 g |
| CaCO$_3$ | 3 g |
| Glycerol | 40 mL |
| L-Glutamate | 4 g |
| L-Leucine | 2 g |
| Yeast Extract | 10 g |
| Na$_2$SO$_4$ | 0.71 g |
| MgSO$_4$.7H$_2$O | 0.51 g |
| FeSO$_4$.7H$_2$O | 0.2 g |
| MgCl$_2$.6H$_2$O | 1.02 g |
| CoCl$_2$ | 20 mg |
| Borax | 20 mg |
| (NH$_4$)$_6$Mo$_7$O$_{24}$.4H$_2$O | 36 mg |
| MnSO$_4$.H$_2$O | 24 mg |
| ZnSO$_4$ | 120 mg |
| CuCl$_2$.2H$_2$O | 2.6 mg |

The pH of the media was adjusted to 6.0 and proline and lysine were added to the medium in varying concentrations, as shown in the table below. The inoculated flasks were incubated at 25° C. on a rotary shaker at 200 rpm (2" stroke). After 7 days incubation, the mycelium was recovered by centrifuging the broths at 1300×g for 12 minutes. The mycelelial pellets were extracted 3 times with 3 volumes of acetone by stirring vigorously. HPLC analysis and purification was accomplished according to the procedure described in Example 1. The following table shows the yields of 21-norrapamycin and rapamycin that were obtained by varying the concentrations of proline and lysine.

| YIELD OF 21-NORRAPAMYCIN PRODUCED BY PRECURSOR ENHANCED FERMENTATION | | | |
|---|---|---|---|
| Proline | Lysine | 21-Norrapamycin (mg/L) | Rapamycin (mg/L) |
| 0.6% | 0.05% | 14.6 | 60 |
| 0.6% | 0.1% | 10.6 | 53 |
| 0.6% | 0.0% | 12.6 | 36 |
| 0.4% | 0.05% | 9.5 | 60 |
| 0.3% | 0.05% | 7.4 | 57 |
| 0.2% | 0.05% | 5.0 | 57 |

What is claimed is:

1. A compound which is 21-norrapamycin or a pharmaceutically acceptable salt thereof.

2. A pharmaceutical composition for inducing immunosuppression in a mammal in need thereof which comprises a therapeutically effective amount of 21-norrapamycin and a pharmaceutical carrier.

3. A method of inducing immunosuppression in a mammal in need thereof which comprises administering an immunosuppressive effective amount of 21-norrapamycin to said mammal.

4. A method of treating transplantation rejection; graft vs. host disease; autoimmune diseases; diseases of inflammation; solid tumors; pulmonary inflammation; and disease states involving intimal smooth muscle cell proliferation in a mammal in need thereof; which comprises administering an effective amount of 21-norrapamycin.

5. The method according to claim 4 wherein the transplanted organ is selected from the group consisting of kidney, heart, liver, lung, bone marrow, pancreas (islet cells), cornea, small bowel, skin, and heart valve.

6. The method according to claim 4 wherein the autoimmune disease is selected from the group consisting of lupus, rheumatoid arthritis, diabetes mellitus, myasthenia gravis, and multiple sclerosis.

7. The method according to claim 4 wherein the disease of inflammation is psoriasis, dermatitis, eczema, seborrhea, inflammatory bowel disease, and eye uveitis.

8. The method according to claim 4 wherein the pulmonary inflammation is selected from the group consisting of asthma, chronic obstructive pulmonary disease, emphysema, acute respiratory distress syndrome, and bronchitis.

9. The method according to claim 4 wherein the disease state involving intimal smooth muscle cell proliferation is restenosis.

10. A method of inhibiting transplantation rejection; graft vs. host disease; autoimmune diseases; diseases of inflammation; solid tumors; pulmonary inflammation; and disease states involving intimal smooth muscle cell proliferation in a mammal in need thereof; which comprises administering an effective amount of 21-norrapamycin.

11. The method according to claim 10 wherein the transplanted organ is selected from the group consisting of kidney, heart, liver, lung, bone marrow, pancreas (islet cells), cornea, small bowel, skin, and heart valve.

12. The method according to claim 10 wherein the autoimmune disease is selected from the group consisting of lupus, rheumatoid arthritis, diabetes mellitus, myasthenia gravis, and multiple sclerosis.

13. The method according to claim 10 wherein the disease of inflammation is psoriasis, dermatitis, eczema, seborrhea, inflammatory bowel disease, and eye uveitis.

14. The method according to claim 10 wherein the pulmonary inflammation is selected from the group consisting of asthma, chronic obstructive pulmonary disease, emphysema, acute respiratory distress syndrome, and bronchitis.

15. The method according to claim 10 wherein the disease state involving intimal smooth muscle cell proliferation is restenosis.

16. A method of treating or inhibiting a fungal infection in a mammal in need thereof which comprises administering an effective amount of 21-norrapamycin.

* * * * *